(12) United States Patent
Dey et al.

(10) Patent No.: US 10,561,414 B2
(45) Date of Patent: Feb. 18, 2020

(54) PACKAGE FOR SUTURES AND NEEDLES

(71) Applicant: DS-Technology GmbH, Winnenden (DE)

(72) Inventors: Clifford Dey, Allmersbach im Tal (DE); Martin Lober, Allmersbach im Tal (DE)

(73) Assignee: DS-Technology GmbH, Winnenden (DE)

( * ) Notice: Subject to any disclaimer, the term of this patent is extended or adjusted under 35 U.S.C. 154(b) by 0 days.

(21) Appl. No.: 16/223,366

(22) Filed: Dec. 18, 2018

(65) Prior Publication Data

US 2019/0183488 A1 Jun. 20, 2019

(30) Foreign Application Priority Data

Dec. 19, 2017 (EP) .................................... 17002038

(51) Int. Cl.
*A61B 17/06* (2006.01)
(52) U.S. Cl.
CPC .................. *A61B 17/06133* (2013.01); *A61B 2017/06142* (2013.01)
(58) Field of Classification Search
CPC ............... A61B 17/06133; A61B 2017/06142
USPC ...... 206/63.3, 339, 480, 409, 485, 380, 382, 206/383
See application file for complete search history.

(56) References Cited

U.S. PATENT DOCUMENTS

| 4,424,898 A | * | 1/1984 | Thyen ............. A61B 17/06133 206/380 |
| 4,961,498 A | | 10/1990 | Kalinski et al. |
| 4,967,902 A | | 11/1990 | Sobel et al. |
| 5,230,424 A | * | 7/1993 | Alpern ............. A61B 17/06133 206/227 |
| 5,655,652 A | | 8/1997 | Sobel et al. |
| 6,047,815 A | | 4/2000 | Cerwin et al. |

(Continued)

FOREIGN PATENT DOCUMENTS

| DE | 10 2010 055048 A1 | 6/2012 |
| EP | 2 172 157 A1 | 4/2010 |

(Continued)

OTHER PUBLICATIONS

European Search Report in 17002038.2-1122, dated Jun. 20, 2018.

*Primary Examiner* — Chun Hoi Cheung
(74) *Attorney, Agent, or Firm* — Collard & Roe, P.C.

(57) ABSTRACT

A surgical sutures package includes a base having top and bottom surfaces, an outer periphery, and a longitudinal axis. An outer wall extending upwardly from the periphery has inner and outer surfaces and a top, the inner surface including bulges extending from the base top surface. An inner wall extending upwardly from the base top surface has inner and outer surfaces and a top. There is a suture channel cover having top and bottom surfaces and an outer periphery having a profiled surface corresponding to the profiled base outer wall inner surface. A cover outer edge opening forms a suture port having first and second ends. The suture track area to retain suture is formed between the outer wall inner surface and the inner wall outer surface of the base. The cover has a central recessed area having an outer periphery corresponding to the base inner wall inner surface.

11 Claims, 4 Drawing Sheets

(56) References Cited

U.S. PATENT DOCUMENTS

| | | | |
|---|---|---|---|
| 6,135,272 A * | 10/2000 | Sobel | A61B 17/06133 206/380 |
| 6,463,719 B2 | 10/2002 | Dey et al. | |
| 7,637,369 B2 * | 12/2009 | Kennedy | A61B 17/06133 206/63.3 |
| 2001/0004966 A1 * | 6/2001 | Warnecke | A61B 17/06133 206/63.3 |
| 2003/0010655 A1 * | 1/2003 | Alpern | A61B 17/06133 206/63.3 |
| 2004/0129591 A1 * | 7/2004 | Koseki | A61B 17/06133 206/380 |
| 2007/0227914 A1 * | 10/2007 | Cerwin | A61B 17/06133 206/63.3 |
| 2010/0078336 A1 * | 4/2010 | Reyhan | A61B 17/06114 206/63.3 |
| 2010/0163435 A1 * | 7/2010 | Fischer | A61B 17/06114 206/204 |
| 2012/0267263 A1 * | 10/2012 | Fischer | A61B 17/06114 206/206 |
| 2013/0264226 A1 * | 10/2013 | Prikril | A61B 17/06133 206/206 |
| 2015/0366559 A1 * | 12/2015 | Lee | A61B 17/06133 206/63.3 |

FOREIGN PATENT DOCUMENTS

| | | |
|---|---|---|
| EP | 3 095 392 A1 | 11/2016 |
| WO | 2013/049400 A1 | 4/2013 |

* cited by examiner

PACKAGE FOR SUTURES AND NEEDLES

CROSS REFERENCE TO RELATED APPLICATIONS

Applicant claims priority under 35 U.S.C. § 119 of European Application No. 17 002 038.2 filed Dec. 19, 2017, the disclosure of which is incorporated by reference.

BACKGROUND OF THE INVENTION

1. Field of the Invention

This invention relates to packages for surgical sutures and needles. Conventional surgical suture and needle packages serve several useful functions, including protecting the needles and sutures during handling, shipping, and storage. In addition, the packages facilitate access and release of the needles and sutures during surgery or other medical procedures prior to application with a minimum of force to dispense. The packages may be used for surgical sutures armed with surgical needles or for unarmed surgical sutures without needles.

2. Description of the Related Art

Packaging for surgical sutures with or without needles is well known in the art. There are two types of packages that have been conventionally used for surgical needles and sutures. One type of package is a paper folder package wherein a medical grade paperboard is folded and cut into a plurality of panels. The suture is then wound onto a panel, and the package is then assembled by first folding the panels into a desired configuration, and then locking the panels in place using slits and locking tabs which have been cut into the panels.

Another type of suture package which has been used is a tray package having a winding channel. These tray packages typically have an oval shape with outer and inner walls forming an oval winding channel. The packages are typically moulded from plastics. The packages are mounted onto a winding fixture and sutures are then wound into the winding channel. Suture packages typically have a needle park member for mounting and securing a surgical needle if a surgical needle is mounted to the sutures. Conventional needle parks can consist of foam members, or equivalent retention structures. The needle park members can also be utilized for mounting one end of a suture wound into the winding channel.

U.S. Pat. No. 4,961,498 discloses a two-piece suture package having an oval winding channel. U.S. Pat. No. 4,967,902 discloses a one-piece channel suture package having a plurality of door members which retain the suture in the channel. U.S. Pat. No. 5,230,424 discloses a package having a substantially square shape and having a square shaped suture channel wherein a plurality of cantilevered doors are mounted to an inner wall to maintain sutures in the channel. U.S. Pat. No. 5,655,652 discloses a package having an oval-shaped winding channel with a top friction plate member in lieu of doors or cantilevered doors.

U.S. Pat. No. 6,135,272 discloses a plurality of cantilevered cover door or petal members with spaces in between. These door members have a disadvantage of deforming if the stylus is moving at a high speed therefore limiting the winding speed. They also have a disadvantage of allowing the smaller diameter suture to escape through the spaces in between these door members.

WO 2013/049400 A1 discloses a suture package having two halves. The interior of the body portion is provided with a pair of posts in one half of the body portion and a corresponding pair of mating bosses in the other half of the body portion. When the two halves of the base are pressed together, the posts fit into the bosses in a press fit or snap fit manner to secure the two halves together. The posts and bosses also provide a structure around which the suture strands may be wrapped.

EP 2 172 157 A1 discloses a suture package for retaining a barbed suture including a suture retaining member with an outer wall and an inner wall. The inner wall is radially spaced from the outer wall and defines a suture retaining area therebetween. The outer wall includes a plurality of inwardly extending tabs configured to engage a cover. The suture package further includes a cover configured to be received within the outer wall of the suture retaining member and to selectively engage the inwardly extending tabs formed thereon.

EP 3 095 392 A1 discloses a package for sutures having a winding channel created by having an outside wall and an inner row of cylindrical standoff members to form a channel for sutures. The package has a base member and a flat cover ember that is mounted to the base member by a plurality of snap locks located on top of the cylindrical standoff members. The edge of the base member has cover locking tabs along the outside wall.

Although the suture tray packages of the prior art are adequate and effective for their intended use, there are disadvantages associated with such packages. An example of one type of problem which may occur is suture "hang-up" when the surgeon attempts to withdraw the suture from the package or when the suture is very hard to withdraw or has a high dispense force. Accordingly, there is a need in this art for novel suture tray packages having winding channels which are readily adaptable to high-speed packaging processes running at over 1200 rpm which overcome the disadvantages of the prior art packages, including problems associated with suture withdrawal. Accordingly, there is a need in this art for novel suture tray packages having a larger suture track volume for the larger sized sutures. Furthermore, there is a need in this art for novel suture tray packages having the capability to contain the micro sutures such as USP 10-0 in the suture channel.

SUMMARY OF THE INVENTION

Proceeding from this previously known prior art, it is an object of the present invention to provide a novel tray package having a winding channel which can be run at a winding speed exceeding 1200 rpm for packaging surgical sutures.

It is yet a further object of the present invention to provide a novel suture tray package which facilitates the withdrawal of sutures from the package with a minimal dispensing force of less than 0.3 Newtons.

It is still a further object of the present invention to provide a novel suture tray package that is of a three piece construction with a plastic bottom and a plastic top along with a paper label for its identification and for desiccant properties.

It is still yet a further object of the present invention to provide a novel suture channel that allows for less memory of the suture after the suture is dispensed.

The suture package according to the invention is produced by the features of the main claim. Appropriate developments of the invention are subject matter of further claims following the main claim.

Accordingly, a suture package is disclosed. The suture package has a base member having a top surface, a bottom surface, an outer periphery and a longitudinal axis. An outer wall extends upwardly about the periphery of said base member, said outer wall having an inner surface, an outer surface, and a top. The inner surface of the outer wall is a profiled surface consisting of a plurality of bulges extending from the top surface of the base member. An inner wall extends upwardly from the top surface of said base member, said inner wall having an inner surface, an outer surface, and a top.

There is also a suture channel cover member preferably made of plastic for mounting to the base member. The suture channel cover member has a top surface, a bottom surface and an outer periphery. The outer periphery has a profiled surface corresponding to the profiled surface of the outer wall of the base member. A port exit opening having a first end and a second end is located in the outer track wall and forms a suture port.

A suture track area to retain suture is formed in between the inner surface of the outer wall and the outer surface of the inner wall of the base member. The cover member has a recessed area in its middle, said recessed area having an outer periphery corresponding to the inner surface of the inner wall of the base member.

This kind of suture package will allow for high speed winding in excess of 1200 rpm due to its flat one piece design of the base member without impact points on flaps or petals that are biased downwards like the current state of the art. The flat design without flaps can retain the smaller sutures down to USP 10-0 due to zero openings between the petals or doors that are in the current state of the art.

These and other features and advantages of the present invention will become more apparent from the following description and accompanying drawings.

The cover member can mounted to the base member to form the package of the present invention by aligning a plurality of fastener pins extending downwardly from the bottom surface of the cover member with corresponding precision holes extending though the top surface of the base member. The fastener pins may be deformed by using ultrasonic sound, for example. It is also possible to leave the fastener pins unchanged. This forms a suture channel between the inner surface of the outer wall of the base member, the top surface of the base member, the outer surface of the inner wall of the base member, and the bottom surface of the suture cover member.

The fastener pins can be arranged at the periphery of the recessed area of the cover member. In this case, the precision holes should be arranged parallel to the inner surface of the inner wall of the base member.

The profiled surface of the outer wall may consist of a plurality of bulges extending from the top surface of the base member to the top of the outer wall. Those bulges may be D shaped vertical members. The length of the D shaped vertical members may vary in one package. The D shaped vertical members should protrude at least one millimeter from the outer wall of the base member in order to provide an interlocking barrier that will contain sutures down to a size of 10/0 and keep them within the package.

The top of the inner wall may have a profiled surface consisting of a plurality of indentations. There may also be an inner wall extending downwardly from the bottom surface of the cover member, said inner wall having an inner surface, an outer surface, and a top. At least in sections, said outer surface of the inner wall of the cover member may have tab members corresponding to the indentations of the top of the inner wall of the base member.

The package may comprise a plurality of air slots in the suture track area of the base member.

The base member may be transparent. This enables the user of the package to better see the location of the suture and the needle. Furthermore, the kind of suture and needle can be seen through the transparent base member.

The cover member may comprise holes for receiving the suture winding pins. These holes may be positioned in the recessed area of the cover member.

The package may have an oval configuration.

There may be at least one hook member and at least one catching recess for fixing the cover member to the base member. Preferably, the at least one hook member can be arranged at the bottom surface of the cover member and the at least one catching recess can be arranged at the base member.

The preferred material for the package is HDPE Dow 25455N with 3% slip as this material reduces the force to dispense by 60% compared to other HDPE like Dow 25055. An optional paper top suture cover may be utilized to complete the assembled package. This paper top works as a desiccant. This assembly is completed after the suture is wound into the channel.

The package has 80% more volume in the suture channel to allow for larger sutures (USP 2 and 3 up to 120 centimeters long) above the current state of the art which will accept up to USP (1 metric 4) 90 centimeters long only.

Needle park means may be located interior the recessed area of the cover member and extending upwardly from the top surface of the cover member for retaining a surgical needle. The needle park means may be located in a second recessed area of the cover member, said second recessed area being part of the first recessed area. In this case, there may be an opening in the base member, the shape of said opening corresponding to the shape of the second recessed area of the cover member.

The package may already comprise a suture wound into the winding channel and a surgical needle mounted in the needle park means.

Further advantages and features of the invention can be gathered from the features which are further specified in the claims and from the following exemplary embodiments.

BRIEF DESCRIPTION OF THE DRAWINGS

In the following text, the invention will be described and explained in greater detail using the exemplary embodiment which is shown in the drawings.

DETAILED DESCRIPTION OF THE PREFERRED EMBODIMENT

Figure 1:
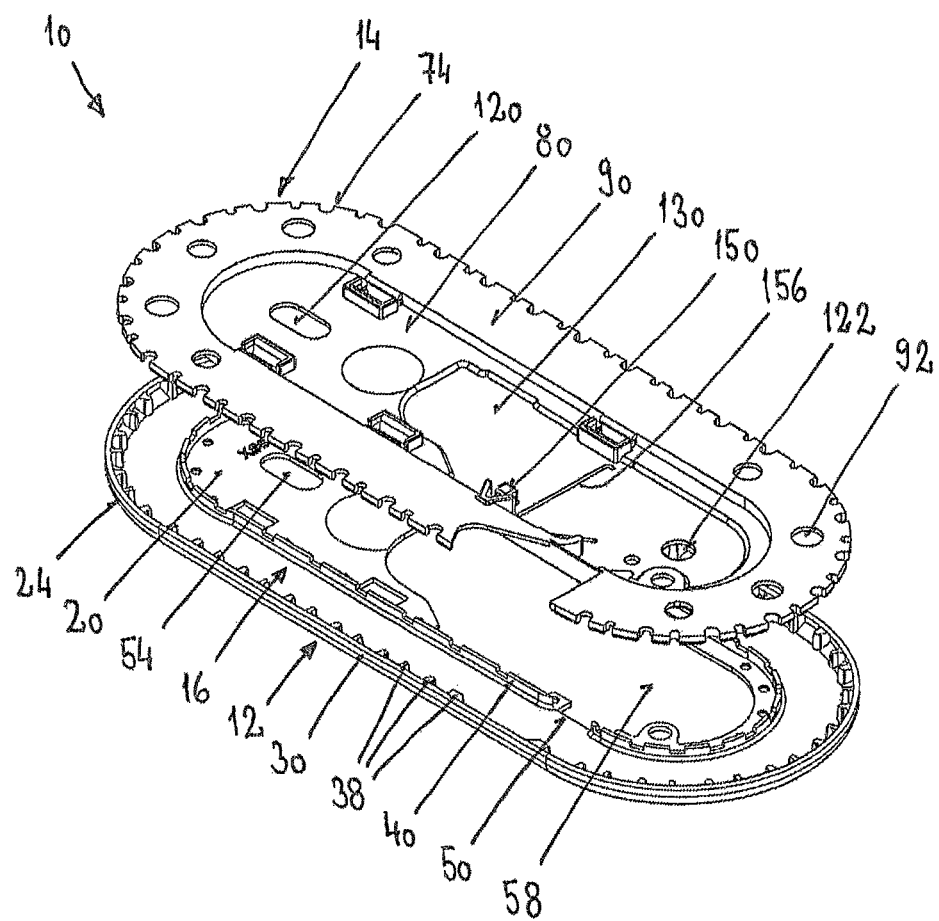
FIG. 1 shows an exploded perspective view of a package of the present invention without a needle and a suture mounted therein.
Figure 4:
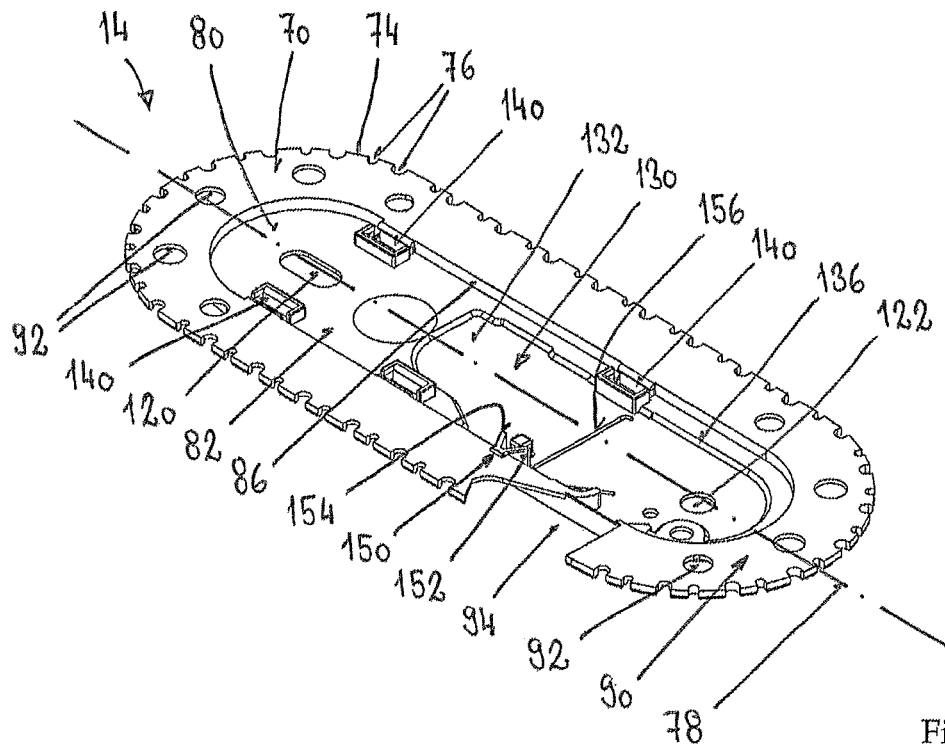
FIG. 4 shows a perspective view of the top surface of the cover member of the package in FIG. 1.
Figure 5:
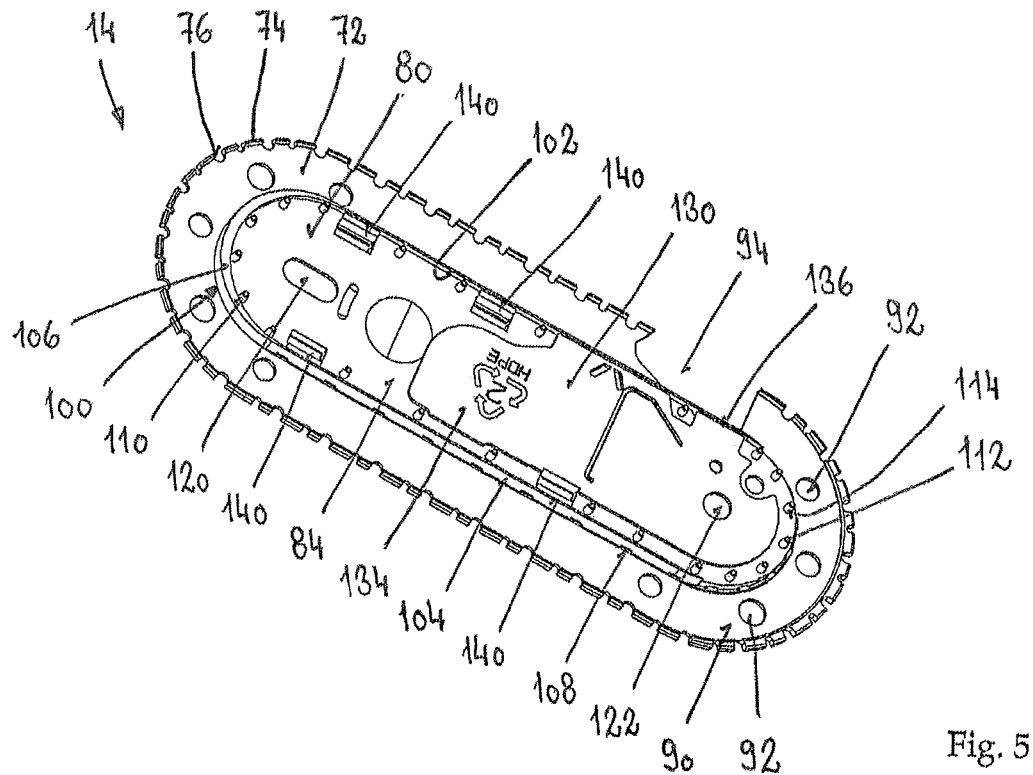
FIG. 5 is a perspective view of the bottom surface of the cover member of the package in FIG. 1.
Figure 6:
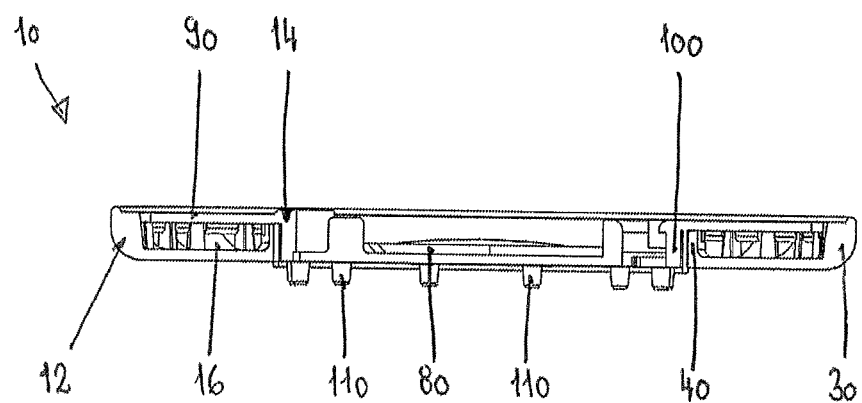
FIG. 6 shows a cross section through the package in FIG. 1 showing the suture track area.

The package 10 according to a first embodiment of the present invention is illustrated in FIGS. 1 to 6. As seen in FIGS. 1 and 6, the package 10 has a base member 12 and a suture channel cover member 14.

Figure 2:
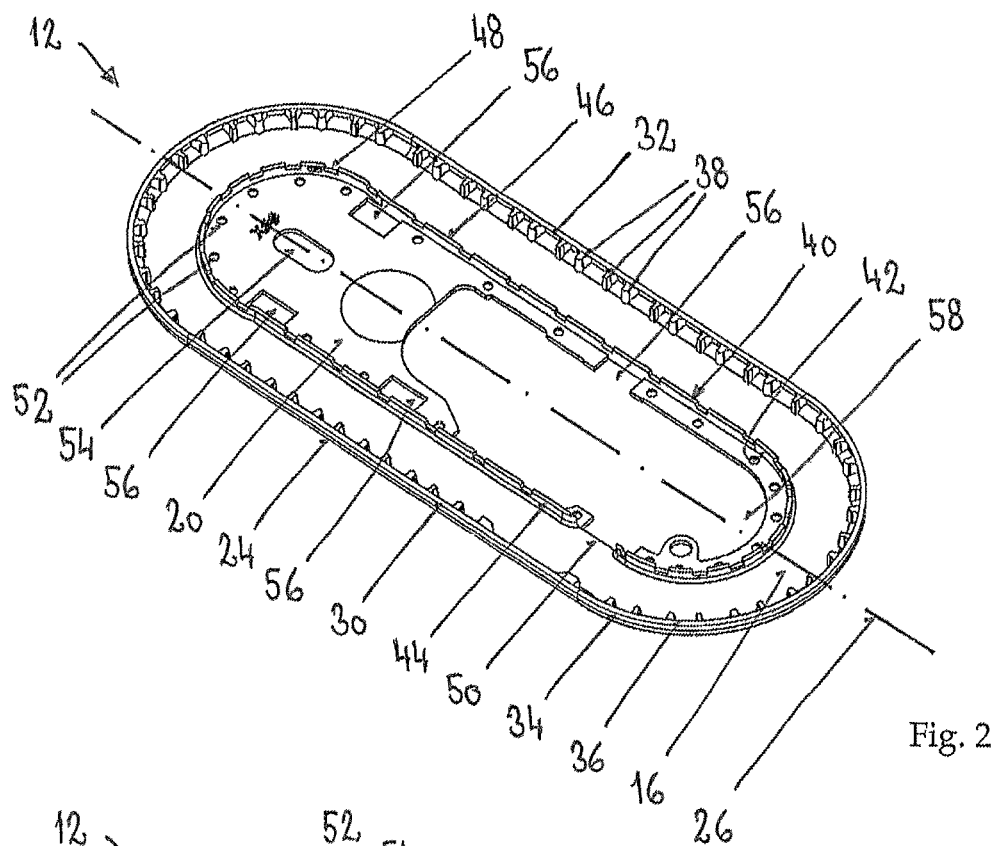
FIG. 2 shows a perspective view of the top surface of the base member of the package in FIG. 1.
Figure 3:
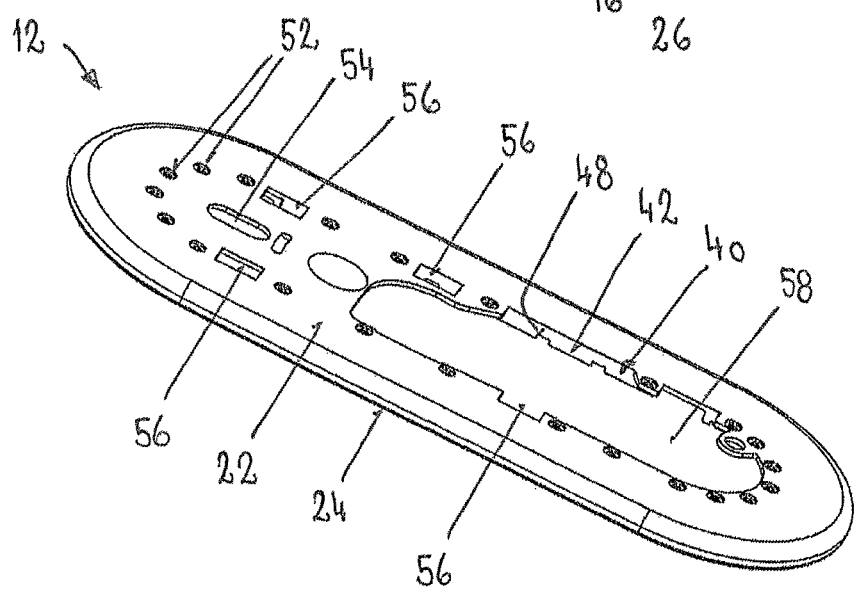
FIG. 3 shows a perspective view of the bottom surface of the base member of the package in FIG. 1.

Referring now in more detail to FIGS. 2 and 3, the base member 12 is seen to have a top surface 20 and a bottom surface 22. The base member 12 is also seen to have an outer periphery 24. The base member 12 is seen to be a substantially flat and substantially oval shaped member having a longitudinal axis 26. However, although it is desired that the base member 12 along with the package 10 be oval shaped, other configurations can be used including circular, polygonal, square with rounded corner, and the like and combinations thereof and equivalents thereof.

Extending upwardly about the periphery 24 of the base member 12 is an outer wall 30. Outer wall 30 is seen to have a bottom, an inner surface 32, an outer surface 34, and a top 36. The inner surface 32 of the outer wall 30 is a profiled surface having a plurality of D shaped bulges 38 extending from the top surface 20 of the base member 12 to the top 36 of the outer wall 30. The D shaped bulges 38 protrude from the outer wall 30 at a minimum of one millimeter.

There can be optional notches at the top 36 of the outer wall 30 of the base member 12. Theses notches are there to keep the base member 12 flat.

An inner wall 40 is seen to extend upward from the top surface 20 of the base member 12. Inner wall 40 is seen to have a bottom, an inner surface 42, an outer surface 44, and a top 46. The top 46 of the inner wall 40 is a profiled surface consisting of a plurality of indentations 48. The inner wall 40 and the outer wall 30 are approximately equispaced to each other, forming a suture track area (winding channel) 16 for a suture between them. The top 46 of the inner wall 40 lies beneath the top 36 of the outer wall 30. Therefore, the top 46 of the inner wall 40 can define the position when the cover member 14 is pushed down onto the base member 12 to the lowest possible level. Furthermore, the inner wall 40 can ease the withdrawal of the suture.

There is a gap 50 in the inner wall 40. This gap 50 is needed for the suture to reach the winding channel after the needle is placed in the middle of the package 10.

Extending through the bottom of the base member 12 are a plurality of precision holes 52. The precision holes 52 are located interior to the inner wall 40. Also extending through the bottom of the base member 12 is the oval drive pin locating hole 54. The drive pin locating hole 54 is seen to be disposed along the longitudinal axis 26 at one end of the base member 12 still interior to the inner wall 40. Also extending through the bottom of the base member 12 are four catching recesses 56 for fixing the cover member 14 to the base member 12. The catching recesses 56 are arranged near the inner surface 42 of the inner wall 40 of the base member 12. However, although it is desired that the catching recesses 56 be rectangular, other configurations can be used including oval, circular, polygonal, square with rounded corner, and the like and combinations thereof and equivalents thereof.

Furthermore, there is an opening 58 in the bottom of the base member 12. The opening 58 includes one of the catching recesses 56 and is positioned so that the gap 50 leads into the opening 58. The opening 58 covers only the middle of the base member 12 interior to the inner wall 40. Nevertheless, the opening 58 may reach the inner surface 42 of the inner wall 40 in sections.

In contrast to the embodiment according to FIGS. 1 to 6, a plurality of air slots could be extending through the bottom of the base member 12. Those air slots should be located between the outer wall 30 and the inner wall 40.

Referring now to FIGS. 4 and 5, the suture channel cover member 14 is seen to be illustrated. The suture channel cover member 14 has a top surface 70, a bottom surface 72, and a periphery 74. The D shaped bulges 38 of the outer wall 30 of the base member 12 have a mirrored cut in the outer periphery 74 of the cover member 14. Those matching indentations 76 in the cover member 14 provide—when assembled—an interlocking barrier that will contain sutures down to a size of 10/0 and keep them within the package 10. The cover member 14 is seen to be a substantially flat and substantially oval shaped member having a longitudinal axis 78.

The cover member 14 has a recessed area 80 in its middle. The recessed area is seen to have a top surface 82, a bottom surface 84, and an outer periphery 86 corresponding to the inner surface 42 of the inner wall 40 of the base member 12. The depth of the recessed area 80 is chosen so that—when assembled—the bottom surface 84 of the recessed area 80 lies upon the top surface 20 of the base member 12 (see FIG. 6).

In between the outer periphery 74 of the cover member 14 and the outer periphery 86 of the recessed area an oval ring section 90 is formed which covers the suture track area 16. Interior this ring section 90 there is a multiplicity of suture winding pin holes 92 extending though the cover member 14. The preferred shape of the suture winding pin holes 92 is circular but other shapes can be utilized such as oval, octagonal, semi-circular, polygonal, triangular, combinations thereof and equivalents thereof and the like. Furthermore, the suture exit port 94 is seen to be contained in the ring section 90 of the cover member 14. When assembled, the ring suture exit port 94 is located above the gap 50 of the inner wall 40 of the base member 12.

In FIG. 5 an inner wall 100 is seen to extend downward from the bottom surface 84 of the recessed area 80. Inner wall 100 is seen to have a bottom, an inner surface 102, an outer surface 104, and a top 106. The inner wall 100 is located at the outer periphery of the recessed area 80 of the cover member 14. There is a plurality of tab members 108 at the outer surface 104 of the inner wall 100. Said tab members 108 correspond to the indentations 76 of the top 46 of the inner wall 40 of the base member 12.

Also extending downwardly from the bottom surface 84 of the recessed area 80 are fastener pins 110. The fastener pins 110 have flat tops 112. The fastener pins 110 are seen to preferably have a cylindrical surface 114, but they may also have flat outer surfaces. If desired, the fastener pins 110 may have other configurations for outer surfaces including semi-circular, polygonal, oval, triangular, of combinations thereof and equivalents thereof and the like. A combination of fastener pins 110 with flat and with cured outer surfaces is also possible. When the package 10 is assembled, the fastener pins 110 mate with the precision holes 52 of the base member 12. Therefore, the diameter and the shape of the precision holes 52 is determined by the shape of the fastener pins 110.

In order to lock the cover member 14 to the base member 12 the fastener pins 110 may be deformed by using ultrasonic sound, for example. This flattens and broadens the top 112 of the fastener pins 110. After this deformation of the top 112 of the fastener pins 110, the precision holes 52 of the base member 12 cannot slip off the fastener pins 110 so the cover member 14 is securely locked to the base member 12.

The pin winding holes 120 and 122 are seen to be contained at opposite ends of the cover member 14. The pin winding holes 120 and 122 are seen to extend through the cover member 14 and to be disposed in the cover member 14 along its longitudinal axis 78, toward either end. Pin winding hole 120 is oval in shape, whereas pin winding hole 122 is of circular shape. However, other geometric shapes can be utilized. The oval pin winding hole 120 lines up with drive pin locating hole 54 of the base member 14. Oval pin winding hole 120 is located interior the recessed area 80 of the cover member 14. The circular pin winding hole 122 lines up with the opening 58 of the base member 12. Circular pin winding hole 122 is located interior a second recessed area 130 of the cover member 14, said second recessed area 130 also being part of the first recessed area 80.

The second recessed area 130 is seen to have a top surface 132, a bottom surface 134, and an outer periphery 136 corresponding to the shape of the opening 58 of the base member 12. The depth of the second recessed area 130 is chosen so that—when assembled—the top surface 132 of the second recessed area 130 aligns with the top surface 20 of the base member 12.

Also extending downwardly from the bottom surface 84 of the recessed area 80 are four hook members 140. The hook members 140 are seen to line up with the catching recesses 56 of the base member 12 in order to fix the cover member 14 to the base member 12.

To maintain the control of the small needles needle park means 150 are located interior the second recessed area 130 extending upwardly from the top surface 132 of said second recessed area 130. In FIG. 4 the needle park means 150 are shown in their preferred configuration with a vertical cantilevered member 152 having a V shaped notch 154 that leaves a small land to contact a needle and hold it in place. In contrast to the embodiment shown in the drawings there can be more than one cantilevered member 152 in order to accommodate different sizes of surgical needles. An optional slit in the bottom of the second recessed area 130 of the cover member 14 can form the tab lifting member 156.

The packages 10 of the present invention are assembled in the following manner. In order to mount sutures having surgical needles mounted to one end in the package 10, the base member 12 is mounted into a conventional, rotatable winding fixture such that the winding pins of the winding fixture are inserted through the pin winding holes 120, 122. The needle is placed into the needle park means 150. Next, the suture is threaded out of the suture exit port 94 into the winding channel 16. The suture is guided into the package 10 by a suture control arm which lifts the cover member 14 about 0.05 inches and runs between the suture cover member 14 and the base member 12 as it is rotated in the fixture such that the suture is completely wound into the suture track 16 as the package 10 is rotated. This may be repeated with additional sutures and additional needles. A printed lid can then be attached to the base member 12 and the cover member 14. The package 10 containing the wound suture and the needle may then be placed in a conventional pouch or package for conventional sterilization treatments such as gaseous sterilants, autoclaving, radiation and the like.

When used by the physician in a surgical procedure, the package 10 is placed into a sterile field. Using a conventional needle grasper, the surgeon pushes down the tab lifting member 156 and the needle can be grasped and removed from the needle park means 150. Needle and suture are then pulled away from the package 10 and the suture exits through suture exit port 94.

The base member 12 of the packages 10 of the present invention may be manufactured from conventional mouldable materials. It is especially preferred to use polyolefin materials such as polyethylene and polypropylene, other thermoplastic materials, and polyester materials such as nylon, and equivalents thereof. The preferred material for both the base member 12 and the cover member 14 is HPDE Dow 25455N. Preferably, the base members 12 of the present invention are injection moulded, however, the base members 12 may be formed by other conventional processes and equivalents thereof included thermo-forming. If desired, the packages 10 may be manufactured as individual assemblies or components which are then assembled.

The sutures and needles that can be packaged in the packages 10 of the present invention include conventional surgical needles and conventional bio-absorbable and non-absorbable surgical sutures and equivalents thereof. The packages 10 of the present invention are useful to package small diameter sutures such as USP 10-0 which were previously difficult to package in tray packages because the suture ends or tails were coming out of the suture track area and therefore causing sealing problems. These problems have been overcome using the packages 10 of the present invention. Moreover, the memory after dispensing has shown to be reduced by approximately 50%.

The packages 10 of the present invention are also useful to package large diameter sutures such as USP 2 and USP 3 and longer lengths of sutures that do not fit in the packages of the current state of the art.

What is claimed is:

1. A package (10) for surgical sutures, comprising:
    a base member (12) having a top surface (20), a bottom surface (22), an outer periphery (24) and a longitudinal axis (26);
    an outer wall (30) extending upwardly from the periphery (24) of said base member (12), said outer wall (30) having an inner surface (32), an outer surface (34), and a top (36), the inner surface (32) of the outer wall (30) being a profiled surface comprising a plurality of bulges (38) extending from the top surface (20) of the base member (12);
    an inner wall (40) extending upwardly from the top surface (20) of said base member (12), said inner wall (40) having an inner surface (42), an outer surface (44), and a top (46);
    a cover member (14) having a top surface (70), a bottom surface (72) and an outer periphery (74), the outer periphery (74) having a profiled surface (76) corresponding to the profiled surface of the inner surface (32) of the outer wall (30) of the base member (12);
    an opening (94) in the outer edge of the cover member (14) forming a suture port having a first end and a second end; and
    a suture track area (16) to retain suture, said suture track area (16) being formed in between the inner surface (32) of the outer wall (30) and the outer surface (44) of the inner wall (40) of the base member (12);
    wherein the cover member (14) has a recessed area (80) in its middle, said recessed area (80) having an outer periphery (86) corresponding to the inner surface (42) of the inner wall (40) of the base member (12);
    further comprising needle park means (150) located interior the recessed area (80) of the cover member (14) and extending upwardly from the top surface (82) of the cover member (14) for retaining a surgical needle;
    wherein
    the needle park means (150) are located in a second recessed area (130) of the cover member (14);
    there is an opening (58) in the base member (12); and
    the shape of said opening (58) corresponds to the outer periphery (136) of the second recessed area (130) of the cover member (14).

2. The package according to claim 1 further comprising
a plurality of fastener pins (110) extending downwardly from the bottom surface (72) of the cover member (14); and
a plurality of precision holes (52) extending through the top surface (20) of the base member (12) to lock said base member (12) to the fastener pins.

3. The package according to claim 2 wherein
the fastener pins (110) are arranged at the outer periphery (86) of the recessed area (80) of the cover member (14); and
the precision holes (52) are arranged parallel to the inner surface (42) of the inner wall (40) of the base member (12).

4. The package according to claim 1 wherein the bulges (38) of the profiled surface of the outer wall (30) of the base member (12) are D shaped vertical members.

5. The package according to claim 4 wherein the D shaped vertical members (38) protrude at least one millimeter from the outer wall (30) of the base member (12).

6. The package according to claim 1 wherein the top (46) of the inner wall (40) is a profiled surface comprising a plurality of indentations (48).

7. The package according to claim 6 further comprising an inner wall (100) extending downwardly from the bottom surface (84) of the cover member (14), said inner wall (100) having an inner surface (102), an outer surface (104), and a top (106);
said outer surface (104) of the inner wall (100) of the cover member (14) having at least in sections tab members (108) corresponding to the indentations (48) of the top (46) of the inner wall (40) of the base member (12).

8. The package according to claim 1 additionally comprising holes (120, 122) through the cover member (14) for receiving suture winding pins.

9. The package according to claim 1 additionally comprising at least one hook member (140) and at least one catching recess (56) for fixing the cover member (14) to the base member (12).

10. The package according to claim 9 wherein
the at least one hook member (140) is arranged at the bottom surface (72) of the cover member (14); and
the at least one catching recess (56) is arranged at the base member (12).

11. The package according to claim 1 further comprising
a suture wound into the suture track area (16); and
a surgical needle mounted in the needle park means (150).

\* \* \* \* \*